United States Patent
Huber et al.

(10) Patent No.: US 12,428,383 B2
(45) Date of Patent: Sep. 30, 2025

(54) GAS-PHASE PROCESS FOR THE CONVERSION OF GLYCOLALDEHYDE WITH AN AMINATING AGENT

(71) Applicant: BASF SE, Ludwigshafen am Rhein (DE)

(72) Inventors: Tatjana Huber, Ludwigshafen am Rhein (DE); Martin Ernst, Ludwigshafen am Rhein (DE); Johann-Peter Melder, Ludwigshafen am Rhein (DE); Stephanie Jaegli, Ludwigshafen am Rhein (DE); Thomas Krug, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 943 days.

(21) Appl. No.: 17/617,503

(22) PCT Filed: Jun. 2, 2020

(86) PCT No.: PCT/EP2020/065199
§ 371 (c)(1),
(2) Date: Dec. 8, 2021

(87) PCT Pub. No.: WO2020/249427
PCT Pub. Date: Dec. 17, 2020

(65) Prior Publication Data
US 2022/0234991 A1    Jul. 28, 2022

(30) Foreign Application Priority Data

Jun. 11, 2019 (EP) .................. 19179444
Jun. 11, 2019 (EP) .................. 19179445
Jun. 11, 2019 (EP) .................. 19179449

(51) Int. Cl.

| | | |
|---|---|---|
| C07C 29/154 | (2006.01) | |
| C07C 209/16 | (2006.01) | |
| C07C 209/26 | (2006.01) | |
| C07C 209/62 | (2006.01) | |
| C07C 209/84 | (2006.01) | |
| C07C 213/02 | (2006.01) | |
| C07C 213/04 | (2006.01) | |
| C07C 213/08 | (2006.01) | |
| C07C 213/10 | (2006.01) | |
| C07D 251/04 | (2006.01) | |

(52) U.S. Cl.
CPC .......... *C07D 251/04* (2013.01); *C07C 29/154* (2013.01); *C07C 209/16* (2013.01); *C07C 209/26* (2013.01); *C07C 209/62* (2013.01); *C07C 209/84* (2013.01); *C07C 213/02* (2013.01); *C07C 213/04* (2013.01); *C07C 213/08* (2013.01); *C07C 213/10* (2013.01)

(58) Field of Classification Search
None
See application file for complete search history.

(56) References Cited

U.S. PATENT DOCUMENTS

| | | |
|---|---|---|
| 4,322,568 A | 3/1982 | Weiss |
| 4,503,260 A | 3/1985 | Auvil et al. |
| 4,677,213 A | 6/1987 | Kitagawa et al. |
| 6,147,261 A | 11/2000 | Knifton et al. |
| 6,534,441 B1 | 3/2003 | Bartley et al. |
| 7,750,189 B2 | 7/2010 | Kubanek et al. |
| 2004/0022912 A1 | 2/2004 | Majerski et al. |
| 2007/0249871 A1 | 10/2007 | Almeida Lenero et al. |
| 2008/0081931 A1 | 4/2008 | Puckette et al. |
| 2009/0012333 A1 | 1/2009 | Almeida Lenero et al. |
| 2011/0172430 A1 | 7/2011 | Ernst et al. |

FOREIGN PATENT DOCUMENTS

| | | |
|---|---|---|
| CN | 107011194 A | 8/2017 |
| DE | 4400591 A1 | 7/1995 |
| EP | 0514692 A2 | 11/1992 |
| EP | 1106600 A2 | 6/2001 |
| EP | 1697291 A1 | 9/2006 |
| EP | 2346602 B1 | 3/2014 |
| JP | 03-246248 A | 11/1991 |
| JP | 03-279342 A | 12/1991 |
| WO | 2011/082967 A1 | 7/2011 |
| WO | 2011/082994 A1 | 7/2011 |

OTHER PUBLICATIONS

International Search Report and Written Opinion received for PCT Patent Application No. PCT/EP2020/065199, mailed on Aug. 18, 2020, 7 pages.
C. R. Vitasari, "Extraction Of Bio-Based Glycolaldehyde From Wood-Derived Pyrolysis Oils", Doctoral Thesis, Technische Universiteit Eindhoven, 2012, 149 pages.
European Search Report for EP Patent Application No. 19179444.5, Issued on Nov. 25, 2019, 2 pages.
European Search Report for EP Patent Application No. 19179445.2, Issued on Dec. 6, 2019, 3 page.
European Search Report for EP Patent Application No. 19179449.4, Issued on Dec. 3, 2019, 3 pages.

(Continued)

*Primary Examiner* — Renee Claytor
*Assistant Examiner* — Jennifer C Sawyer
(74) *Attorney, Agent, or Firm* — Faegre Drinker Biddle & Reath LLP

(57) ABSTRACT

A process for the conversion of glycolaldehyde with an aminating agent in the presence of hy-5 drogen and of a catalyst, wherein the conversion is carried out in the gas phase.

12 Claims, No Drawings

(56) References Cited

OTHER PUBLICATIONS

International Preliminary Report on Patentability received for PCT Patent Application No. PCT/EP2020/065199, mailed on Dec. 23, 2021, 6 pages.
Liang, et al., "Production of Primary Amines by Reductive Amination of Biomass-Derived Aldehydes/Ketones", Angewandte Chemie International Edition, vol. 56, Issue 11, Feb. 3, 2017, pp. 3050-3054.
Liang, et al., "Production of Primary Amines by Reductive Amination of Biomass-Derived Aldehydes/Ketones", Angewandte Chemie, vol. 129, Issue 11, Feb. 3, 2017, pp. 3096-3100.
Mohan, et al., "Pyrolysis of Wood/Biomass for Bio-oil:? A Critical Review", Energy & Fuels, vol. 20, Issue 3, Mar. 10, 2006, pp. 848-889.
Pelckmans, et al., "Catalytic reductive aminolysis of reducing sugars: elucidation of reaction mechanism", ACS Catalysis, vol. 8, Issue 5, Apr. 6, 2018, pp. 4201-4212.

GAS-PHASE PROCESS FOR THE CONVERSION OF GLYCOLALDEHYDE WITH AN AMINATING AGENT

CROSS-REFERENCE TO RELATED APPLICATIONS

This application is a national stage application (under 35 U.S.C. § 371) of PCT/EP2020/065199, filed Jun. 2, 2020, which claims benefit of European Application Nos. 19179444.5, 19179445.2, and 19179449.4, all filed Jun. 11, 2019, all four of which are incorporated herein by reference in their entirety.

The present invention relates to processes for the manufacture of ethyleneamines and ethanolamines by conversion of glycolaldehyde and an aminating agent in the gas-phase.

Glycolaldehyde appears to be a useful raw material for the production of ethyleneamines and ethanolamines.

U.S. Pat. No. 6,534,441 describes a process for reductive amination of lower aliphatic alkane derivatives using a nickel/rhenium catalyst. A possible feedstock mentioned in the description is glycolaldehyde.

German patent application DE-A1-4400591 describes a process for preparing amino alcohols by reacting hydroxy carbonyl compounds with hydrogen and an aminating agent at temperatures of 0 to 300° C. and pressures of 1 to 400 bar over a catalyst which comprises 50 to 100% by weight of ruthenium. Glycolaldehyde is disclosed as suitable hydroxy carbonyl compound which can be employed in the process.

The conversion of hydroxy alkanals to diamines in the presence of ammonia and hydrogen in the presence of catalysts which comprise nickel or cobalt is disclosed in U.S. Pat. No. 6,147,261. U.S. Pat. No. 6,147,261 teaches that hydroxy alkanals are very reactive and tends to oligomerization and polymerization.

Although U.S. Pat. No. 6,147,261, DE-A1-4400591 and U.S. Pat. No. 6,534,441 mention the use of glycolaldehyde as a feedstock in a reaction with an aminating agent, the specific reaction demonstrated by examples has not been described.

CN107011194 discloses a method for conversion of glycolaldehyde with different aminating agents, such as ammonia, methylamine, ethylamine and butylamine in the presence of hydrogen using noble metal catalysts which comprised rare earth metals.

The conversion of glycolaldehyde with aminating agents, such as ammonia, in the presence of hydrogen was disclosed in WO2011/082994. Due to glycolaldehyde's tendency to form oligomers, such as the dimer 2,5-dihydroxy-1,4-dioxane, a six-membered ring compound formed having a high thermodynamic stability, the conversion required the pre-activation of non-noble metal amination catalysts to achieve high conversions.

The effect of catalyst pre-activation was later confirmed by Liang et al. (Angew. Chem. 2017, 129, 3096-3100) who studied the conversion of glycolaldehyde with ammonia in the presence hydrogen and Ru-catalysts.

Pelckmans et. Al (ACS Catal. 2018, 8, 4201-4212) studied the reductive amination of various sugars with dimethylamine in the presence of hydrogen and different metal catalysts. It was proposed that glycolaldehyde is formed as an intermediate during the reductive aminolysis of sugars. The authors therefore studied the reaction behavior of pure glycolaldehyde with dimethylamine and hydrogen over a nickel catalyst as a model reaction. High conversions to TMEDA and DMEOA were obtained in MeOH-solutions.

WO2011/082967 discloses the amination of glycolaldehyde with the aminating agents MEA and DEA in the presence of hydrogen and amination catalysts to yield alkanolamines.

The aforementioned applications disclose the conversion of glycolaldehyde in the liquid phase in the presence of solvents.

Within the frame of the present invention it has been found, that the conversion of glycolaldehyde and aminating agents in the liquid phase in strongly aqueous solvents, especially water, results in lower conversions and lower yields ethyleneamines and/or ethanolamines. However, the use of such solvents, especially water, is highly desired from a processing point of view, since glycolaldehyde and aminating agents are often manufactured and produced in form or their aqueous solutions. In addition, water is a readily available and inexpensive solvent and has a high solvent power for glycolaldehyde and aminating agents, such as ammonia. Further, treatment and recycling of water is comparatively unproblematic and can be carried out in waste treatment plant allowing the treated water to be discharged to the environment or to be used in other applications.

It was therefore object of the present invention to provide a process for the manufacture of ethyleneamines and ethanolamines in a high yields and high conversions allowing the handling of glycolaldehyde and aminating in aqueous solvents, especially water.

The object of the present invention was achieved by a process for the manufacture of ethyleneamines and ethanolamines by conversion of glycolaldehyde with an aminating agent in the presence of hydrogen and of a catalyst, wherein the conversion is carried out in the gas phase.

In the process according to the invention, glycolaldehyde is used.

Glycolaldehyde is commercially available and can be prepared, for example, by oxidizing ethylene glycol (see, for example, JP 3246248 and JP 3279342).

Glycolaldehyde is preferably synthesized by reaction of formaldehyde with carbon monoxide and hydrogen, as described, for example, in US 2009012333, US 2008081931, US 2007249871, EP 1697291, U.S. Pat. Nos. 4,503,260 and 4,322,568.

More preferably, glycolaldehyde can also be obtained from the cracking of aqueous solutions of organic feedstocks, such as sugars or woods, at high temperatures.

In a more preferred embodiment, a glycolaldehyde solution is obtained by the hydrous thermolysis of sugars, such as the process disclosed in US 2004/0022912, which is hereby incorporated by reference. Such processes preferably yield streams of glycolaldehyde and water.

In a further preferred embodiment, a glycolaldehyde solution is obtained by the pyrolysis of wood, such as the processes disclosed by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958).

Glycolaldehyde has a strong tendency to form oligomers in the pure state or in solutions. In particular the dimer 2,5-dihydroxy-1,4-dioxane, a six-membered ring compound having a high thermodynamic stability, is formed.

Unless otherwise explicitly stated, all indications of weights and molar ratios of glycolaldehyde in this specification refer to monomeric glycolaldehyde, irrespective of whether the glycolaldehyde used in the conversion is present in the monomeric, dimeric or oligomeric form.

A further starting material used in the process according to the invention is an aminating agent.

The aminating agents used in the hydrogenating amination of alcohols, aldehydes or ketones in the presence of hydrogen may be either ammonia or primary or secondary aliphatic or cycloaliphatic or aromatic amines.

The aminating agent is preferably a nitrogen compound of the formula I

in which $R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $C_{3-30}$-dialkylaminoalkyl, aryl, aralkyl such as $C_{7-20}$-aralkyl, and alkylaryl such as $C_{7-20}$-alkylaryl, or together are —$(CH_2)_j$—X—$(CH_2)_k$—, X is $CH_2$, $CHR^3$, oxygen (O), sulfur (S) or $NR^3$, $R^3$ is hydrogen (H), alkyl such as $C_{1-4}$-alkyl, alkylphenyl such as $C_{7-40}$-alkylphenyl, j, k are each integers from 1 to 4.

Preference is given to aminating agents in which $R^1$ and $R^2$ are each—the same or different—alkyl, such as $C_{1-20}$-alkyl, preferably $C_{1-12}$-alkyl, more preferably $C_{1-8}$-alkyl and most preferably $C_{1-4}$-alkyl.

In a preferred embodiment, the following mono- and dialkylamines are used as aminating agents: monomethylamine, dimethylamine, monoethylamine, diethylamine, n-propylamine, di-n-propylamine, iso-propylamine, di-iso-propylamine, iso-propyl-ethylamine, n-butylamine, di-n-butylamine, s-butylamine, di-s-butylamine, iso-butylamine, di-iso-butylamine, n-pentylamine, di-n-pentylamine, s-pentylamine, di-s-pentylamine, iso-pentylamine, di-iso-pentylamine, n-hexylamine, di-n-hexylamine, s-hexylamine, di-s-hexylamine, iso-hexylamine and di-iso-hexylamine.

Especially preferred aminating agents are monomethylamine, monoethylamine, dimethylamine and diethylamine. Very particular preference is given to using dimethylamine and diethylamine as aminating agents.

The conversion of glycolaldehyde with the aminating agent is conducted in the presence of hydrogen.

The hydrogen is generally used in technical grade purity. The hydrogen can also be used in the form of a hydrogen-comprising gas, i.e. in mixtures with other inert gases, such as nitrogen, helium, neon, argon or carbon dioxide. Preference is given, however, to using pure hydrogen or essentially pure hydrogen, for example hydrogen with a content of more than 99% by weight of hydrogen, preferably more than 99.9% by weight of hydrogen, more preferably more than 99.99% by weight of hydrogen, especially more than 99.999% by weight of hydrogen.

The conversion of glycolaldehyde with the aminating agent is conducted in the presence of a catalyst.

The catalysts may in principle comprise nickel, cobalt, iron, copper, chromium, manganese, copper, molybdenum, tungsten and/or other metals of groups 8 and/or 9 and/or 10 and/or 11 of the periodic table of the elements Preference is given to using catalysts which comprise at least one metal selected from the group consisting of Cu, Co, Ni, Pd, Pt, Ru, Rh, Ag, Au, Re and Ir.

More preference is given to using catalysts which comprise at least one metal selected from the group consisting of Cu, Co, Ni, Pd, Pt and Ru.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

The catalyst can be a supported or unsupported catalyst.

Suitable support materials are carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

In a preferred embodiment of the invention, catalysts of the Raney type are being used.

As Raney catalysts, Raney cobalt catalysts, Raney nickel catalysts and/or Raney copper catalysts are preferably used. Raney cobalt catalysts are particularly preferred.

In a further preferred embodiment of the invention the catalysts are prepared by reduction of a catalyst precursor, in which the aforementioned metals are present in the form of oxygen comprising compounds, such as their oxides, carbonates or hydrogencarbonates.

The catalyst precursors can be prepared by known processes, for example by precipitation, precipitative application or impregnation.

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying.

Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or the doping elements, such as cobalt nitrate or cobalt chloride. Thereafter, the impregnated support material is generally dried and optionally calcined.

The impregnation can also be affected by the so-called "incipient wetness method", in which the support material is moistened with the impregnating solution up to a maximum of saturation according to its water absorption capacity. However, the impregnation can also be affected in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be affected simultaneously with all metal salts or in any desired sequence of the individual metal salts.

In a further preferred embodiment, catalyst precursors are prepared by means of a coprecipitation of all of their components. To this end, in general, a soluble compound of the corresponding active component and of the doping elements, and optionally a soluble compound of a support material is admixed with a precipitant in a liquid while heating and while stirring until the precipitation is complete.

The liquid used is generally water.

Useful soluble compounds of the active components typically include the corresponding metal salts, such as the nitrates, sulfates, acetates or chlorides of the aforementioned metals.

The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides, are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates formed in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be affected, for example, by adjusting the precipitation catalyst to a particular particle size by grinding.

After the grinding, the catalyst precursor obtained by precipitation reactions can be mixed with shaping assistants such as graphite or stearic acid and processed further to shaped bodies. Common processes for shaping are described, for example, in Ullmann [Ullmann's Encyclopaedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granules, spheres, cylinders or grains. Common processes for shaping are, for example, extrusion, tableting, i.e. mechanical pressing, or pelletizing, i.e. compacting by circular and/or rotating motions.

The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as the oxides, mixed oxides and/or hydroxides. The catalyst precursors thus prepared can be stored as such.

The catalyst which is used in the process according to the invention is obtained by reducing catalyst precursors which have been prepared by impregnation or precipitation as described above after the calcination or conditioning.

The reduction of the dry, generally pulverulent catalyst precursor can be performed at elevated temperature in a moving or stationary reduction oven.

The reducing agent used is typically hydrogen or a hydrogen-comprising gas.

The hydrogen is generally used in technical grade purity. The hydrogen can also be used in the form of a hydrogen-comprising gas, i.e. in admixtures with other inert gases, such as nitrogen, helium, neon, argon or carbon dioxide. The hydrogen stream can also be recycled into the reduction as cycle gas, optionally mixed with fresh hydrogen and optionally after removing water by condensation.

The catalyst precursor is preferably reduced in a reactor in which the shaped catalyst bodies are arranged as a fixed bed. The catalyst precursor is more preferably reduced in the same reactor in which the conversion of glycolaldehyde with the aminating agent is carried out.

Alternatively, the catalyst precursor can be reduced in a separate fluidized bed reactor in the fluidized bed.

The catalyst precursor is generally reduced at reduction temperatures of 50 to 600° C., especially of 100 to 500° C., more preferably of 150 to 450° C.

The partial hydrogen pressure is generally from 1 to 300 bar, especially from 1 to 200 bar, more preferably from 1 to 100 bar, where the pressure figures here and hereinafter are based on the absolute measured pressure.

The duration of the reduction is preferably 1 to 20 hours and more preferably 5 to 15 hours.

During the reduction, a solvent can be supplied in order to remove water of reaction which forms and/or in order, for example, to be able to heat the reactor more rapidly and/or to be able to better remove the heat during the reduction. In this case, the solvent can also be supplied in supercritical form.

Suitable solvents used may be the above-described solvents. Preferred solvents are water; ethers such as methyl tert-butyl ether, ethyl tert-butyl ether, dioxane or tetrahydrofuran. Particular preference is given to water or tetrahydrofuran. Suitable solvents likewise include suitable mixtures.

The catalyst precursor can also be reduced in suspension, for example in a stirred autoclave.

The temperatures are generally within a range from 50 to 300° C., especially from 100 to 250° C., more preferably from 120 to 200° C.

The reduction in suspension is generally performed at a partial hydrogen pressure of 1 to 300 bar, preferably from 10 to 250 bar, more preferably from 30 to 200 bar. Useful solvents include the aforementioned solvents.

The duration of the reduction in suspension is preferably 5 to 20 hours, more preferably 8 to 15 hours.

The catalyst can be handled under inert conditions after the reduction. The catalyst can preferably be handled and stored under an inert gas such as nitrogen, or under an inert liquid, for example an alcohol, water or the product of the particular reaction for which the catalyst is used. If appropriate, the catalyst must then be freed of the inert liquid before commencement of the actual reaction.

The storage of the catalyst under inert substances enables uncomplicated and safe handling and storage of the catalyst.

After the reduction, the catalyst can also be contacted with an oxygen-comprising gas stream such as air or a mixture of air with nitrogen. This affords a passivated catalyst. The passivated catalyst generally has a protective oxide layer. This protective oxide layer simplifies the handling and storage of the catalyst, such that, for example, the installation of the passivated catalyst into the reactor is simplified.

After passivation, the catalyst is usually activated. A catalyst can be activated by reducing a passivated catalyst. A passivated catalyst can be reduced as described above by treating the passivated catalyst with hydrogen or a hydrogen-comprising gas. The reduction conditions correspond generally to the reduction conditions employed in the reduction of the catalyst precursors. The activation generally eliminates the protective passivation layer.

An activated catalyst has to be handled under inert conditions during and after the activating reduction thereof.

The activated catalyst is preferably handled and stored under an inert gas, such as nitrogen, or under an inert liquid, for example an alcohol, water or the product of the particular reaction for which the catalyst is used. If appropriate, the activated catalyst then has to be freed of the inert liquid before commencement of the actual reaction.

Activation of the catalyst can also occur in situ during conversion step in which glycolaldehyde is converted with an aminating agent.

According to the invention, glycolaldehyde is converted with the aminating agent in the gas phase.

In the context of the present invention, "reaction or conversion in the gas phase" means that the reaction conditions, such as pressure and temperature, are adjusted such that glycolaldehyde and the aminating agent are present in the gas phase and flow around the catalyst in gaseous form.

Suitable reactors for the gas phase conversion of glycolaldehyde with an aminating agent are generally tubular reactors and fluidized bed reactors.

The catalyst may be arranged as a moving bed or fixed bed in the tubular reactors.

Particular preference is given to converting glycolaldehyde with the aminating agent in a tubular reactor in which the catalyst is arranged in the form of a fixed bed.

In a further particular embodiment, glycolaldehyde is converted with the aminating agent in a fluidized bed reactor.

Since the process of the present invention is conducted in the gas-phase, it is preferred that the glycolaldehyde is provided to the inventive process in the gaseous form.

In a preferred embodiment, the reactants are transferred into the gas phase by evaporation of the reactants in their pure form or by evaporation of mixtures of the reactants and one or more solvents.

In a preferred embodiment, glycolaldehyde is provided in gaseous form by evaporation of pure glycolaldehyde and/or the aminating agent is provided in gaseous form by evaporation of the pure aminating agent.

In a more preferred embodiment, each reactant is transferred into the gas phase by evaporation of a mixture each reactant in one or more solvents.

Preferably the one or more solvents are selected from the group consisting of water, alcohols, non-cyclic or cyclic ethers, polyalkylethers and alkoxypolyalkylethers.

More preferably the one or more solvents are selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme) or bis(2-methoxyethyl) ether (diglyme).

It is generally preferred, that glycolaldehyde is transferred into the gas phase in the absence of the aminating agent and vice versa. It has been found that if both glycolaldehyde and the aminating agent are present together in the liquid phase prior to evaporation, glycolaldehyde and the aminating agent may form higher boiling compounds.

Accordingly, it is preferred that the content of aminating agent in the glycolaldehyde or its solvent mixtures which are to be subjected to evaporation is less than 30 percent by weight, preferably less than 10 percent by weight and most preferably less than 1 percent by weight, based on the total weight of glycolaldehyde, the one or more solvents and any aminating agent present in those mixtures. However, as previously stated, it is preferred that the evaporation of glycolaldehyde is conducted in the absence of any aminating agent.

Accordingly, it is preferred that the content of glycolaldehyde in the aminating agent or its solvent mixtures which are to be subjected to evaporation is less than 30 percent by weight, preferably less than 10 percent by weight and most preferably less than 1 percent by weight, based on the total weight of aminating agent, the one or more solvents and any glycolaldehyde present in those mixtures. However, as previously stated, it is preferred that the evaporation of aminating agents is conducted in the absence of any glycolaldehyde.

Most preferably, the glycolaldehyde is transferred into the gas phase from mixtures in which the fraction of water in the one or more solvents in the mixture is in the range of 25 to 100 percent by weight, preferably 50 to 100 percent by weight and more preferably 75 to 100 percent by weight.

Most preferably glycolaldehyde is transferred into the gas phase by evaporation of a mixture of glycolaldehyde and solvent, in which water is the only solvent.

The weight content of glycolaldehyde in the mixtures of one or more solvents is preferably in the range of 1 to 90 percent by weight, based on the total weight of glycolaldehyde and the one or more solvents.

In a preferred embodiment, the weight content of glycolaldehyde in the mixtures of one or more solvents in the range of 2 to 50 percent by weight, and more preferably 5 to 35 and most preferably 5 to 20 percent by weight, based on the total weight of glycolaldehyde and the one or more solvents.

Most preferably, the aminating agent is transferred into the gas phase from mixtures in which the fraction of water in the one or more solvents in the mixture is in the range of 50 to 100 percent by weight, preferably 60 to 100 percent by weight and more preferably 80 to 100 percent by weight.

Most preferably the aminating agent is transferred into the gas phase by evaporation of a mixture of aminating agent and solvent, in which water is the only solvent.

Most preferably, the aminating agent is transferred into the gas phase by evaporation of the pure compound.

The weight content of aminating agent in the mixtures of one or more solvents is preferably in the range of 1 to 90 percent by weight, more preferably 0 to 80 percent by weight and most preferably 25 to 75 percent by weight, based on the total weight of aminating agent and the one or more solvents.

Evaporation of each reactant or their respective solvent mixtures may be affected by operations well-known in the arts, e.g. by heating the liquids to temperatures above the boing point of the reactants and/or by reducing the pressure and or by passing a stream of gas over the liquid reactants or solvent mixtures.

Preferably, the reactants transferred into the gas phase by evaporation by heating the reactant or its solvent mixtures in a stream of gas.

The gas is preferably hydrogen or an inert gas, such as nitrogen or a noble gas, such as He, Ne Ar, Kr or Xe. Preferably, the gas is hydrogen, nitrogen or a mixture thereof.

Evaporators which can be used for the evaporation of glycolaldehyde and their respective solvent mixtures are natural or forced circulation evaporators, falling film evaporators, rising film (or long tube vertical) evaporators, climbing and falling-film plate evaporators, multi-effect evaporators, and agitated thin film evaporators. The evaporation can also be affected by a flash evaporation.

In a more preferred embodiment, the reactants are provided to the process of the invention in the gaseous form, by feeding reactants which are obtained from a manufacturing process which provides the reactants in their gaseous form.

Preferably, glycolaldehyde is provided in the gaseous form by feeding gaseous effluents obtained from a manufacturing process of glycolaldehyde.

Such gaseous glycolaldehyde is preferably obtained by the cracking of aqueous solutions of organic feedstocks, such as sugar or wood, at high temperatures More preferably, glycolaldehyde is the gaseous form is obtained by the hydrous thermolysis of sugars, such as the process disclosed in US 2004/0022912, which is hereby incorporated by reference or by the pyrolysis of wood as described by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958), which are also incorporated herein by reference.

Preferably, the concentration of glycolaldehyde in product streams coming from such processes is in the range of 5 to 90 percent by weight, most preferably 10 to 80 percent by weight and most preferably 15 to 70 percent by weight.

The streams obtained by such processes may comprise other oxygenates, such as formaldehyde, hydroxyacetone (acetol), dihydroxyacetone, glyoxal, methylglyoxal (pyruvaldehyde), acetic acid, levulinic acid, propionic acid, acrylic acid, methanol, acetone and formic acid.

Preferably, the aminating agents are provided in the gaseous form by feeding gaseous effluents obtained from a manufacturing process of the aminating agents. Such gaseous streams may be obtained during the refining of the aminating agents. For example, the production of ammonia or lower alkyl amines provides ammonia or the lower alkyl amines in the gas-phase when such aminating agents are separated from higher boiling components at the top of a distillation column. Instead of condensing, the gaseous stream obtained at the top of a distillation column, the gaseous aminating agent can be directly provided to the process of the invention.

Glycolaldehyde which has been provided in its gaseous form and aminating agent which has been provided in its gaseous form can be fed separately to the reactor or they can be mixed to obtain a mixed feed stream.

The proportion of glycolaldehyde which is present during the process of the invention is generally in the range of 0.01% to 10% by volume, preferably 0.1% to 8% by volume, even more preferably 0.5% to 5% by volume.

The molar ratio of aminating agent to glycolaldehyde which is present during the process of the invention is generally in the range from 1:1 to 100:1, preferably 5:1 to 75:1, more preferably 10:1 to 50:1, especially preferably 12.5:1 to 40:1.

The molar ratio of hydrogen to glycolaldehyde which is present during the process of the invention is generally in the range from 10:1 to 500:1, preferably 20:1 to 400:1, more preferably 50:1 to 250:1 and even more preferably 75:1 to 200:1.

The proportion of solvents in the gas stream which is present during the process of the invention is generally in the range from 0% to 20% by volume, preferably 0.1% to 15% by volume, even more preferably 0.5% to 10% by volume. The solvent which are present during the process are in preferably those solvents (i) which are used to prepare the solutions from which the reactants are evaporated, or (ii) which come together with the reactants from a gaseous effluent stream from their manufacturing process, e.g. gaseous glycolaldehyde stemming from the hydrous thermolysis of sugars generally comprises water. Most preferably, the fraction of water in the one or more solvents present in the process is in the range of 50 to 100 percent by weight, preferably 60 to 100 percent by weight and more preferably 80 to 100 percent by weight. Most preferably, water is the only solvent present during the process.

Optionally, the gas stream which is present during the process of the invention comprises an inert gas. Preferred inert gases are noble gases, such as He, Ne, Ar, nitrogen and mixtures thereof. Very particularly preferred inert gases are Ar and nitrogen, or mixtures thereof. The proportion of inert gas in the gas stream which is contacted with the catalyst is generally in the range from 5% to 90% by volume, preferably 10% to 80% by volume, even more preferably 25% to 60% by volume and especially 30% to 50% by volume.

The catalyst loading is preferably in the range of 0.01 to 2 kg/L/h, more preferably 0.025 to 1.5 kg/L/h and more preferably 0.05 to 1 kg/L/h.

Preferably, the reaction of glycolaldehyde with the aminating agent in the gas phase is affected at a pressure in the range from 0.1 to 200 bar (0.01 to 20 MPa), more preferably 0.5 to 100 bar (0.05 to 10 MPa), even more preferably 1 to 50 bar (0.1 to 5 MPa) and especially preferably 1 to 30 bar (0.1 to 3 MPa).

The temperature is preferably in the range from 120 to 600° C., more preferably in the range from 130 to 500° C., even more preferably in the range from 135 to 350° C. and especially preferably in the range from 140 to 270° C.

The product stream obtained from the conversion of glycolaldehyde with the aminating in the process according to the invention may comprise unreacted glycolaldehyde and unreacted aminating agent and hydrogen.

Additionally, the product stream comprises substituted and unsubstituted ethyleneamines, ethanolamines and aminoethylamines.

If the aminating agent is ammonia, the product stream preferably comprises ethylenediamine, monoethanolamine, diethanolamine and triethanolamine.

If the aminating agent is a primary alkylamine, the product stream preferably comprises N-alkyl-ethanolamin, N-alkyl-diethanolamine and dialkylethylendiamine. Accordingly, when methylamine (MA) is used as an aminating agent, the product stream comprises N-methyl-ethanolamine, N-methyl-diethanolamine and dimethyldiethylenediamine.

If the aminating is a secondary alkylamine, the product stream preferably comprises dialkylethanolamine and tetralkylethylenediamine. Accordingly, when dimethylamine (DMA) is used as an aminating agent, the product stream comprises dimethylethanolamine (DMEOA) and tetramethylethylenediamine (TMEDA).

Further, the product stream may comprise one or more solvents.

In addition, the product stream may comprise other components, which were fed to the GA-reactor or which were formed as side-products during the conversion reaction, such as oxygenates, e.g. formaldehyde, hydroxyacetone (acetol), dihydroxyacetone, glyoxal, methylglyoxal (pyruvaldehyde), methanol and acetone.

The output from the reactor optionally comprises the catalyst, which is generally separated from the gaseous components by a suitable apparatus, for example by means of a solids separation which is generally configured as a centrifugal separator (or else cyclone or cyclone separator).

The gaseous output is generally worked up, such that the different components are separated from one another.

For this purpose, the gaseous output is preferably partially condensed, such that hydrogen and any lower boiling aminating agent remain in the gas phase and the other components present in the output are converted to the liquid phase. The gaseous components are generally separated from the liquid components in a gas/liquid separator. The gaseous components can be recycled into the amination reactor individually (after a further workup step) or together.

After hydrogen and any low boiling aminating agents has been separated off, the output from the amination reactor generally comprises aminating agents, unconverted glycolaldehyde, optionally solvents and the amination products as well as other components, such as components introduced together with the reactants streams or side-products formed during the conversion.

Preferably this mixture is subjected to a multistage distillation, in which the products of the reactions or suitable fractions thereof can be obtained in purified form.

Surprisingly, it has been found that the conversion of glycolaldehyde with aminating agents in the gas phase allows the conversion of glycolaldehyde with aminating agents in aqueous environments Within the frame of the present invention it has been found, that the conversion of glycolaldehyde and aminating agents in the liquid phase in water, results in lower conversions and lower yields of ethyleneamines and/or ethanolamines.

The inventive process allows the use of water which is highly desired from a processing point of view, since glycolaldehyde and aminating agents are often manufactured and produced in form of their aqueous solutions.

The conversion of glycolaldehyde in the presence of water has the further advantage that water is a readily available and inexpensive solvent and has a high solvent power for glycolaldehyde. In addition, the treatment and recycling of water is comparatively unproblematic and can be carried out in waste treatment plant allowing the treated water to be discharged to the environment or to be used in other applications.

EXAMPLES

The invention is illustrated by the following examples:

Example 1 (Comparative Example): Liquid Phase Conversion

Before introduction into the autoclave, the passivated catalysts A and B were activated as follows:

In run 1, catalyst A was reduced at 240° C. for 8 h at a partial hydrogen pressure of 1 bar. In run 2, catalyst B was reduced at 200° C. for 8 h at a partial hydrogen pressure of 1 bar.

Subsequently, an electrically heated 300 mL autoclave with a mechanical magnet-coupled stirrer was charged with an aqueous solution of glycolaldehyde (7.5 wt. % or 15 wt. %) under an inert gas atmosphere. Dimethylamine, according to the molar ratio specified in Table 1, was metered in and the mixture was heated to the reaction temperature of 160° C. On attainment of this temperature, the reactor was pressurized to 100 bar by the injection of hydrogen.

The product stream was analyzed by gas chromatography and is reported in Table 1:

TABLE 1

| Run No | GA-Concentration (wt.-%) | Catalyst | Ratio DMA/GA | MEG (%) | DMEOA (%) | TMEDA (%) | Total (%) |
|---|---|---|---|---|---|---|---|
| 1 | 7.5 | A | 19:1 | 0 | 2 | 1 | 3 |
| 2 | 15 | B | 9_1 | 0 | 2 | 1 | 3 |

Example 2: Gas Phase Conversion

A double-walled glass reactor of 1000 mm length, diameter 40 mm with oil heating, a quartz frit at the bottom, an inlet for liquid and gaseous feeds at the top connected to a pump and gaseous feeds (H$_2$, optionally N$_2$ and aminating agent) measured via rotameters, was set up vertically and the outlet (bottom) was connected to a collecting flask. This was mounted with a water cooler and an additional dry-ice cooler. The off-gas was connected to a laboratory hood vent. Into the center of the reactor, a glass tube was put from the top down and a flexible thermocouple was introduced into this tube. The reactor was filled in three layers. First, 400 mL of Raschig rings composed of steel wire mesh (diameter 5 mm) were loaded onto the quartz frit. Then a catalyst (100 mL, see Table 2) was introduced. The height of the catalyst bed was about 80 mm. Above the catalyst bed, 450 mL of Raschig rings were loaded that served as an evaporator and heating zone for the liquid feed and the gas feed. The feed inlet of the aminating agent was positioned centrally about 10 cm above the catalyst bed via a steel capillary that was fixed to the thermocouple. The Raschig ring bed between the inlet of the aminating agent feed and the catalyst ensured thorough mixing of DMA and gaseous GA.

The catalyst was activated prior to the experiment in a stream of hydrogen at a temperature of 240° C.

The tubular reactor was heated up to the reaction temperature indicated in Table 2.

Gaseous DMA was metered from a bottle and introduced via the capillary into the reactor. The amount of DMA in the gas stream corresponds to the amount specified in Table 2.

GA solution was directly fed on top of the evaporator bed in the reactor. Hydrogen was fed into the reactor from the top of the evaporator bed downwards through the reactor at 1 bar. The GA solution evaporated through the combined action of the heating and constant entrainment by hydrogen and the evaporator bed served as a heater for the GA/hydrogen stream. The amount of GA in the gas stream corresponds to the amount specified in Table 2. The concentration of the aqueous GA-solution, from which the GA is evaporated is also given in Table 2.

The combined gas stream of GA and water, hydrogen and aminating DMA passed over the catalyst bed and was partially condensed in the two coolers described above. The condensed material was collected in the collecting flask. Liquid samples were withdrawn regularly from the flask.

The gas hourly space velocity (GHSV) is also given in Table 2.

The composition of the liquid sample was determined by gaschromatography yielding the mass fractions of the major components. Taking into account the amount of condensed product stream and the mass of the glycolaldehyde feed, the yields of the major value products ethylene glycol (MEG), dimethylethanolamine (DMEOA) and tetramethylethylenediamine (TMEDA) were calculated. The results are reported in Table 2.

Catalyst A was a catalyst comprising 45 percent by weight of Cu and 10 percent by weight of Ni on an alumina support. The preparation of the catalyst was carried out according to the Example in EP-B1-2346602.

Catalyst B was catalyst comprising 56 percent by weight of Cu, based on the total weight of the catalyst, on an alumina support, as used in Example 1 of EP-A2-0514692

The comparison of Example 1 with Example 2 shows that the liquid phase conversion of glycolaldehyde with an aminating agent in water delivers only small yields of desired products. The gas phase conversion gives significantly higher yields.

The invention claimed is:

1. A process for the conversion of glycolaldehyde with an aminating agent in the presence of hydrogen and of a catalyst, wherein the conversion is carried out in the gas phase and in the presence of one or more solvents wherein the weight fraction of water in the one or more solvents present during the process is in the range of 50 to 100 percent by weight and wherein the aminating agent is a compound of formula (I)

in which

R$^1$, R$^2$ are hydrogen (H), alkyl, cycloalkyl, alkoxyalkyl, dialkylaminoalkyl, aryl, aralkyl, or alkylaryl, or together are —(CH$_2$)$_j$—X—(CH$_2$)$_k$—, X is CH$_2$, CHR$^3$, oxygen (O), sulfur(S) or NR$^3$, R$^3$ is hydrogen (H), alkyl, or alkylphenyl, j, k are each integers from 1 to 4.

2. The process according to claim 1, wherein the glycolaldehyde is provided to the process in the gaseous form, and wherein the aminating agent is provided to the process in the gaseous form.

3. The process according to claim 2, wherein the glycolaldehyde is provided to the process in the gaseous form by evaporation of glycolaldehyde from mixtures of glycolaldehyde and one or more solvents in which the content of glycolaldehyde is in the range of 2 to 50 percent by weight, based on the total weight of glycolaldehyde and the one or more solvents.

4. The process according to claim 2, wherein the aminating agent is provided to the process in its gaseous form by

TABLE 2

| Run No | GA-Concentration (wt.-%) | Catalyst | Temperature (° C.) | Ratio DMA/GA | Ratio H2/GA | Catalyst Load (kgL/h) | MEG (%) | DMEOA (%) | TMEDA (%) | Total (%) |
|---|---|---|---|---|---|---|---|---|---|---|
| 1 | 7.5 | A | 160 | 19:1 | 191:1 | 0.06 | 0 | 47 | 26 | 73 |
| 2 | 15 | A | 160 | 19:1 | 92:1 | 0.06 | 0 | 33 | 38 | 71 |
| 3 | 15 | A | 160 | 39:1 | 92:1 | 0.05 | 0 | 21 | 47 | 68 |
| 4 | 15 | B | 170 | 19:1 | 91:1 | 0.06 | 0 | 64 | 8 | 71 |
| 5 | 15 | B | 160 | 19:1 | 91:1 | 0.06 | 0 | 66 | 4 | 70 |
| 6 | 15 | B | 160 | 19:1 | 91:1 | 0.06 | 0 | 65 | 3 | 68 |
| 7 | 15 | B | 160 | 9:1 | 91:1 | 0.06 | 0 | 60 | 5 | 65 |
| 8 | 15 | B | 160 | 36:1 | 84:1 | 0.12 | 0 | 71 | 3 | 74 |
| 9 | 15 | B | 160 | 18:1 | 45:1 | 0.12 | 0 | 68 | 4 | 72 |
| 10 | 15 | B | 160 | 12:1 | 56:1 | 0.17 | 1 | 67 | 2 | 70 |
| 11 | 15 | B | 165 | 12:1 | 56:1 | 0.17 | 1 | 74 | 4 | 76 | evaporation of the aminating in its pure form or by evaporation of mixtures of aminating agent in one or more solvents.

5. The process according to claim 2, wherein the glycolaldehyde is provided to the process in the gaseous form by feed gaseous effluents obtained from the manufacture of glycolaldehyde.

6. The process according to claim 5, wherein the glycolaldehyde in its gaseous form is obtained from the hydrous thermolysis of sugars or pyrolysis of wood.

7. The process according to claim 2, wherein the aminating agent which is provided to the process is transferred into its gaseous form in the absence of glycolaldehyde and glycolaldehyde which is provided to the process is transferred into gaseous form in the absence of aminating agent.

8. The process according to claim 2, wherein the gaseous aminating agent and the gaseous glycolaldehyde are provided separately to the process or wherein the gaseous aminating agent and the gaseous glycolaldehyde are mixed to obtain a mixed feed stream.

9. The process according to claim 1, wherein the proportion of glycolaldehyde which is present during the process is in the range of 1 to 50 percent by volume.

10. The process according to claim 1, wherein the molar ratio of glycolaldehyde to aminating agent which is present during the process is in the range to 1:1 to 100 and/or wherein the molar ratio of hydrogen to glycolaldehyde which is present during the process is in the range of 10:1 to 500:1.

11. The process according to claim 1, wherein the proportion of solvent which is present during the process is in the range of 1 to 50 percent by volume.

12. The process according to claim 1, wherein the conversion of glycolaldehyde is carried out at a pressure of 0.01 to 200 bar and/or at a temperature of 120 to 600° C.

* * * * *